United States Patent [19]

Reissenweber et al.

[11] 4,297,491
[45] Oct. 27, 1981

[54] PREPARATION OF 2,3-DIOXO-1,4-BENZOXAZINE DERIVATIVES

[75] Inventors: Gernot Reissenweber, Ludwigshafen; Dietrich Mangold, Neckargemuend, both of Fed. Rep. of Germany

[73] Assignee: BASF Aktiengesellschaft, Fed. Rep. of Germany

[21] Appl. No.: 203,447

[22] Filed: Nov. 3, 1980

[30] Foreign Application Priority Data

Nov. 6, 1979 [DE] Fed. Rep. of Germany ....... 2944696

[51] Int. Cl.³ .......................................... C07D 265/32
[52] U.S. Cl. ............................... 544/105; 424/248.57
[58] Field of Search ........................................ 544/105

[56] References Cited

U.S. PATENT DOCUMENTS 3,238,201  3/1966  Scherrer ................................ 544/94

FOREIGN PATENT DOCUMENTS 1161080  1/1964  Fed. Rep. of Germany ...... 544/104
1013572  12/1960  United Kingdom ................ 544/105

OTHER PUBLICATIONS

Honkanen et al., Chem. Abstracts, vol. 60, col. 1076 e et seq. (1964), (Abst. of Acta Chem. Scand. vol. 14, pp. 1214–1217 (1960).
Alexandrou et al., Chem. Abstracts, vol. 72, Abst. 3465c (1970), (Abst. of J. Chem. Soc. C 1969, pp. 2319–2321).
Dickore et al., Chem. Abstracts, Abst. No. 132645k (1970), (Abst. of Ann. Chem. vol. 733, pp. 70–87 (1970).

Dickore et al., Annalen der Chemie, vol. 733, pp. 70–87 (1970).
Chemical Abstracts, Fifth Decennial Index (1947–1956, vols. 41–50), Subjects Hy-Ly, p. 6820s.

Primary Examiner—John D. Randolph
Attorney, Agent, or Firm—Keil & Witherspoon

[57] ABSTRACT

A process for the preparation of a 2,3-dioxo-1,4-benzoxazine derivative of the formula I

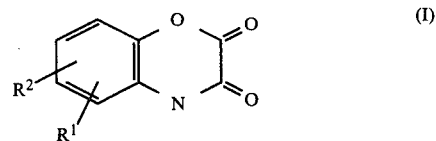

where $R^1$ and $R^2$ are identical or different and each is hydrogen, alkyl, halogen, haloalkyl, alkoxy, haloalkoxy or nitro, by oxidizing an isatin of the formula II

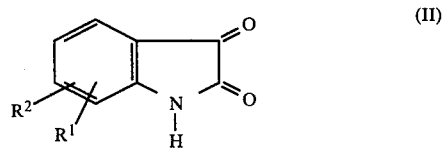

where $R^1$ and $R^2$ have the above meanings, with a peroxydisulfate dissolved or suspended in 30–98% strength sulfuric acid.

The 2,3-dioxo-1,4-benzoxazine derivatives obtainable by the novel process have fungicidal or fungistatic properties.

3 Claims, No Drawings

PREPARATION OF 2,3-DIOXO-1,4-BENZOXAZINE DERIVATIVES

The present invention relates to a process for the preparation of 2,3-dioxo-1,4-benzoxazine derivatives by oxidation of isatins with a peroxydisulfate in a sulfuric acid medium.

The preparation of 2,3-dioxo-1,4-benzoxazines by reacting o-aminophenols with oxalyl chloride has been disclosed (Ann. Chem. 753 (1970), 70–87). 2,3-Dioxo-1,4-benzoxazines are also obtained by reacting o-nitrophenols with an oxalic acid ester chloride and then reducing the nitro group to the amino group, whereupon cyclization to give the 2,3-dioxo-1,4-benzoxazine derivatives takes place, with elimination of alcohol (German Published Application DAS No. 1,161,080). A disadvantage of these processes is that o-aminophenols and o-nitrophenols, especially if they contain additional substituents on the aromatic ring, are in most cases expensive to prepare and that oxalyl chloride and oxalic acid ester chlorides are not readily obtainable industrially.

We have found that a 2,3-dioxo-1,4-benzoxazine derivative of the formula I

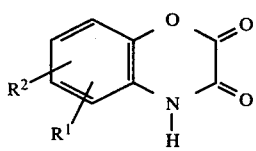

where $R^1$ and $R^2$ are identical or different and each is hydrogen, alkyl, halogen, haloalkyl, alkoxy, haloalkoxy or nitro, is obtained in an advantageous manner by oxidizing an isatin of the formula II

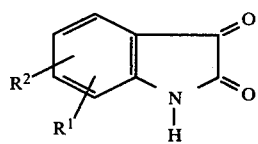

where $R^1$ and $R^2$ have the above meanings, with a peroxydisulfate, dissolved or suspended in 30–98% strength sulfuric acid.

Compared to the conventional processes, the process according to the invention starts from readily obtainable isatins and gives the desired compounds simply and very economically, in high yield and great purity.

The novel process may be used to prepare 2,3-dioxo-1,4-benzoxazine itself and its derivatives with substituents on the benzene nucleus. Suitable substituents $R^1$ and $R^2$ are linear or branched alkyl, alkoxy, haloalkyl or haloalkoxy, especially of 1 to 4 carbon atoms, eg. methyl, ethyl, propyl, butyl, methoxy, ethoxy, i-propoxy, n-butoxy, sec.-butoxy, i-butoxy, trifluoromethyl, difluoromethyl, 2-fluoroethyl, trifluoromethoxy and tetrafluoroethoxy, halogen, eg. chlorine, bromine and fluorine, and nitro.

The benzoxazine derivatives of the formula I are known crop protection agents. For example, 2,3-dioxo-1,4-benzoxazines with chlorine substituents on the benzene nucleus have excellent fungicidal or fungistatic properties (German Published Application DAS No. 1,161,080).

The oxidation is carried out by dissolving or suspending from 1 to 2 moles, preferably from to 1.5 moles, of a peroxydisulfate in from 750 to 3,000 ml, preferably from 1,000 to 2,000 ml of 30–98% strength sulfuric acid and slowly introducing 1 mole of isatin into this solution at from −20° C. to +30° C., preferably at from 0° C. to +10° C. When all has been added, the reaction mixture is stirred for a further 10–30 minutes if 80–98% strength sulfuric acid is used or up to 24 hours if less concentrated sulfuric acid is used and is then poured onto ice. The end product, which is thereby obtained in a crystalline form, can readily be isolated by conventional methods, for example by filtering off or centrifuging.

Suitable oxidizing agents are salts of peroxydisulfuric acid, such as alkali metal peroxydisulfates, eg. sodium peroxydisulfate and potassium peroxydisulfate, or ammonium peroxydisulfate, as well as peroxydisulfuric acid itself.

The nuclear-substituted isatin derivatives used as starting materials are known or can readily be prepared by analogy to conventional processes (Houben-Weyl, Methoden der organ. Chemie, volume VII/4, pages 5–25, Georg Thieme-Verlag, Stuttgart, 1968).

The Examples which follow illustrate the process according to the invention. Parts are by weight.

EXAMPLE 1

103 parts of isatin are introduced slowly into a solution of 190 parts of potassium peroxydisulfate in 1,300 parts of 90% strength sulfuric acid at from 0° C. to 10° C. The mixture is then stirred for 10–20 minutes, after which it is poured onto ice. The product is filtered off and dried, giving 110 parts of 2,3-dioxo-1,4-benzoxazine, of melting point 285° C. (with decomposition).

EXAMPLE 2

14.7 parts of isatin are introduced into a suspension of 29 parts of potassium peroxydisulfate in 280 parts of 30% strength sulfuric acid at room temperature. The reaction mixture is then stirred for 24 hours without cooling, after which it is poured into water. The product is filtered off and dried, giving 11 parts of 2,3-dioxo-1,4-benzoxazine, of melting point 279°–283° C. (with decomposition).

EXAMPLE 3

32.2 parts of 7-methylisatin are introduced into a solution of 56 parts of potassium peroxydisulfate in 450 parts of 92% strength sulfuric acid at from 0° C. to 10° C. The mixture is then stirred for a few minutes, after which it is poured onto ice. The product is filtered off and dried, giving 31.4 parts of 5-methyl-2,3-dioxo-1,4-benzoxazine, of melting point 247°–249° C.

EXAMPLE 4

35 parts of 6,7-dimethylisatin are introduced into a solution of 60 parts of potassium peroxydisulfate in 400 parts of 98% strength sulfuric acid at from 5° C. to 10° C. The mixture is then stirred for 10–20 minutes, after which it is poured onto ice. The product is filtered off and dried, giving 34 parts of 5,6-dimethyl-2,3-dioxo-1,4-benzoxazine, of melting point 278°–284° C. (with decomposition).

The following 2,3-dioxo-1,4-benzoxazines can be prepared similarly: 7-bromo-2,3-dioxo-1,4-benzoxazine, of melting point 318° C. (with decomposition), the yield being 95% of theory; 5,7-dichloro-2,3-dioxo1,4-benzoxazine, of melting point 257° C., the yield being 95% of theory; 7-nitro-5-methyl-2,3-dioxo-1,4-benzoxazine, of melting point 275°–283° C., the yield being 85% of theory; 5-trifluoromethyl-2,3-dioxo-1,4-benzoxazine, of melting point 207°–210° C., the yield being 82% of theory.

We claim:

1. A process for the preparation of a 2,3-dioxo1,4-benzoxazine derivative of the formula I

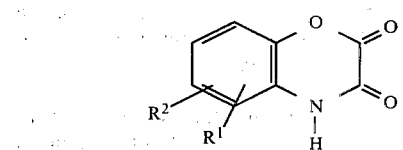

where $R^1$ and $R^2$ are identical or different and each is hydrogen, alkyl, halogen, haloalkyl, alkoxy, haloalkoxy or nitro, wherein an isatin of the formula II

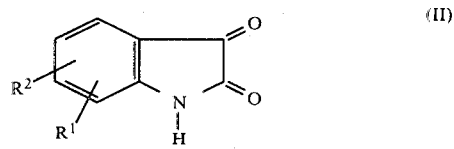

where $R^1$ and $R^2$ have the above meanings, is oxidized with a peroxydisulfate, dissolved or suspended in 30–98% strength sulfuric acid.

2. A process for the preparation of a 2,3-dioxo1,4-benzoxazine derivative of the formula I as claimed in claim 1, wherein the oxidation is carried out with an alkali metal peroxydisulfate.

3. A process for the preparation of a 2,3-dioxo-1,4-benzoxazine derivative of the formula I as claimed in claim 1, wherein 1–2 moles of peroxydisulfate are used per mole of isatin of the formula II.

* * * * *